United States Patent
Chen et al.

(10) Patent No.: US 9,618,452 B2
(45) Date of Patent: Apr. 11, 2017

(54) FLUORESCENCE HYPERSPECTRAL MICROSCOPY SYSTEM FEATURING STRUCTURED ILLUMINATION AND PARALLEL RECORDING COMPRISING A FREQUENCY-DIVIDING REFLECTION ELEMENT

(71) Applicant: National Central University, Taoyuan (TW)

(72) Inventors: Szu-Yu Chen, Taoyuan (TW); Poyu Su, Taoyuan (TW); Chiao-Sheng Lu, Taoyuan (TW); Yu John Hsu, Taoyuan (TW)

(73) Assignee: National Central University, Taoyuan (TW)

( * ) Notice: Subject to any disclaimer, the term of this patent is extended or adjusted under 35 U.S.C. 154(b) by 105 days.

(21) Appl. No.: 14/741,629

(22) Filed: Jun. 17, 2015

(65) Prior Publication Data

US 2016/0320305 A1   Nov. 3, 2016

(30) Foreign Application Priority Data

Apr. 29, 2015  (TW) .............................. 104113747 A

(51) Int. Cl.
   *G01N 21/64*   (2006.01)
   *G01J 3/02*    (2006.01)
   (Continued)

(52) U.S. Cl.
   CPC .......... *G01N 21/6458* (2013.01); *G01J 3/021* (2013.01); *G01J 3/0208* (2013.01); *G01J 3/0229* (2013.01); *G01J 3/0267* (2013.01); *G01J 3/10* (2013.01); *G01J 3/12* (2013.01); *G01J 3/2803* (2013.01); *G01J 2003/282* (2013.01); *G01J 2003/2813* (2013.01);
   (Continued)

(58) Field of Classification Search
   CPC .......... G01N 21/6458; G01N 21/6456; G01N 21/64; G01N 2021/174; G01J 3/0208; G01J 3/4406
   USPC ........ 250/201.3, 559.4–559.46, 559.22, 576; 600/178, 562, 109–118
   See application file for complete search history.

(56) References Cited

U.S. PATENT DOCUMENTS 8,431,389 B2 *  4/2013  Battrell ................ G01N 21/645
                                                        422/82.05

* cited by examiner

*Primary Examiner* — Que T Le
(74) *Attorney, Agent, or Firm* — Juan Carlos A. Marquez; Marquez IP Law Office, PLLC

(57) ABSTRACT

A fluorescence hyperspectral microscopy system featuring structured illumination and parallel recording includes a light projection sub-system, a detection sub-system, and an electrical controller. The light projection sub-system includes a digital light processing (DLP) module for generating linear excitation light, a first lens set, an optical path allocation element, and an objective lens. The detection sub-system includes a second lens set, a frequency-dividing reflection element, a two-dimensional light detector, and a light collection element. With the detection sub-system performing detection in conjunction with the light projection sub-system, and the electrical controller controlling the DLP module, a two-dimensional moving platform, and the two-dimensional light detector, the fluorescence hyperspectral microscopy system provides increased resolution and can obtain accurate information in spatial and spectral dimensions and hence a four-dimensional hyperspectral image of the object under detection.

9 Claims, 6 Drawing Sheets

(51) Int. Cl.
*G01J 3/10* (2006.01)
*G01J 3/12* (2006.01)
*G01J 3/28* (2006.01)

(52) U.S. Cl.
CPC ................ *G01N 2021/6476* (2013.01); *G01N 2021/6478* (2013.01)

FLUORESCENCE HYPERSPECTRAL MICROSCOPY SYSTEM FEATURING STRUCTURED ILLUMINATION AND PARALLEL RECORDING COMPRISING A FREQUENCY-DIVIDING REFLECTION ELEMENT

BACKGROUND OF THE INVENTION

1. Technical Field

The present invention relates to a spectral measurement system and more particularly to a fluorescence hyperspectral microscopy system featuring structured illumination and parallel recording.

2. Description of Related Art

With the advancement of technology, people with imaging needs have higher and higher requirements on precision and the dimensions that a single image can display. To satisfy such requirements, fluorescence microscopy was developed and has found application in biotechnology, materials science, physics, medicine, and so on, as a means of detection.

There are two existing fluorescence microscopy imaging techniques, namely scanning by point-by-point excitation and wide-field illumination with an adjustable filter. The point-by-point excitation scanning technique is generally carried out by confocal microscopy or two-photon fluorescence microscopy and is disadvantaged by its time-consuming recording process and relatively low spectral resolution.

Wide-field illumination with an adjustable filter is lacking in longitudinal resolution and therefore applicable only to relatively thin samples. Not only are the resulting images of relatively low resolution, but also the imaging process is relatively unstable.

Hence, it has been a common goal of development and innovation in the fields of optical spectrum analysis and microscopy imaging to create a useful fluorescence hyperspectral microscopy system which is easy to implement, fast and accurate in spectral detection, and stable in terms of imaging, and which can produce four-dimensional hyperspectral images of high spectral resolution as well as high three-dimensional resolution (e.g., in the X-, Y-, and Z-axis directions).

BRIEF SUMMARY OF THE INVENTION

The present invention is a fluorescence hyperspectral microscopy system featuring structured illumination and parallel recording, wherein the system includes a light projection sub-system, a detection sub-system, and an electrical controller. According to the present invention, detection is carried out by the detection sub-system in conjunction with the light projection sub-system while the electrical controller controls the digital light processing module and two-dimensional moving platform of the light projection sub-system and the two-dimensional light detector of the detection sub-system. Thus, the fluorescence hyperspectral microscopy system provides enhanced resolution and can accurately obtain spatial and spectral information of an object under detection to produce a four-dimensional hyperspectral image.

The present invention provides a fluorescence hyperspectral microscopy system featuring structured illumination and parallel recording, wherein the system includes a light projection sub-system, a detection sub-system, and an electrical controller. The light projection sub-system includes: a digital light processing (DLP) module for generating linear excitation light; a first lens set consisting of at least one lens and configured to condense the linear excitation light into a detection light beam; an optical path allocation element for reflecting the detection light beam in order for the detection light beam to travel along a first path; and an objective lens provided in the first path and configured to receive the detection light beam, focus the detection light beam onto an object under detection on a two-dimensional moving platform, receive a fluorescence signal, which is generated by the object under detection when excited by the detection light beam, and transmit the fluorescence signal along the first path to the optical path allocation element such that the fluorescence signal passes through the optical path allocation element. The detection sub-system includes: a second lens set on which the fluorescence signal passing through the optical path allocation element is incident and which modulates the fluorescence signal to a corresponding collimated light beam and outputs the collimated light beam; a frequency-dividing reflection element for reflecting signals of different frequencies in the collimated light beam at different angles respectively to produce a two-dimensional signal; a two-dimensional light detector for receiving the two-dimensional signal; and a light collection element provided between the frequency-dividing reflection element and the two-dimensional light detector and configured to condense the two-dimensional signal onto the two-dimensional light detector. The electrical controller is electrically connected to and configured to control the DLP module, the two-dimensional moving platform, and the two-dimensional light detector. The electrical controller is also configured to perform a control procedure.

Implementation of the present invention at least involves the following inventive steps:

1. Thanks to the linear excitation light generated and projected by the DLP module, spectral resolution is increased.

2. Thanks to the linear excitation light generated and projected by the DLP module, detection signals are enhanced in spatial (especially longitudinal) resolution.

3. As the DLP module scans fast, the time required for scan sampling is substantially reduced.

4. With the DLP module performing multi-phase detection, the detected signals are enhanced in spatial (especially transverse) resolution.

5. Information in the spectral dimension as well as in three spatial dimensions can be accurately obtained to produce a four-dimensional hyperspectral image of the object under detection.

The features and advantages of the present invention are detailed hereinafter with reference to the preferred embodiments. The detailed description is intended to enable a person skilled in the art to gain insight into the technical contents disclosed herein and implement the present invention accordingly. In particular, a person skilled in the art can easily understand the objects and advantages of the present invention by referring to the disclosure of the specification, the claims, and the accompanying drawings.

BRIEF DESCRIPTION OF THE SEVERAL VIEWS OF THE DRAWINGS

The invention as well as a preferred mode of use, further objectives and advantages thereof will be best understood by reference to the following detailed description of illustrative embodiments when read in conjunction with the accompanying drawings, wherein.

DETAILED DESCRIPTION OF THE INVENTION

Figure 1:
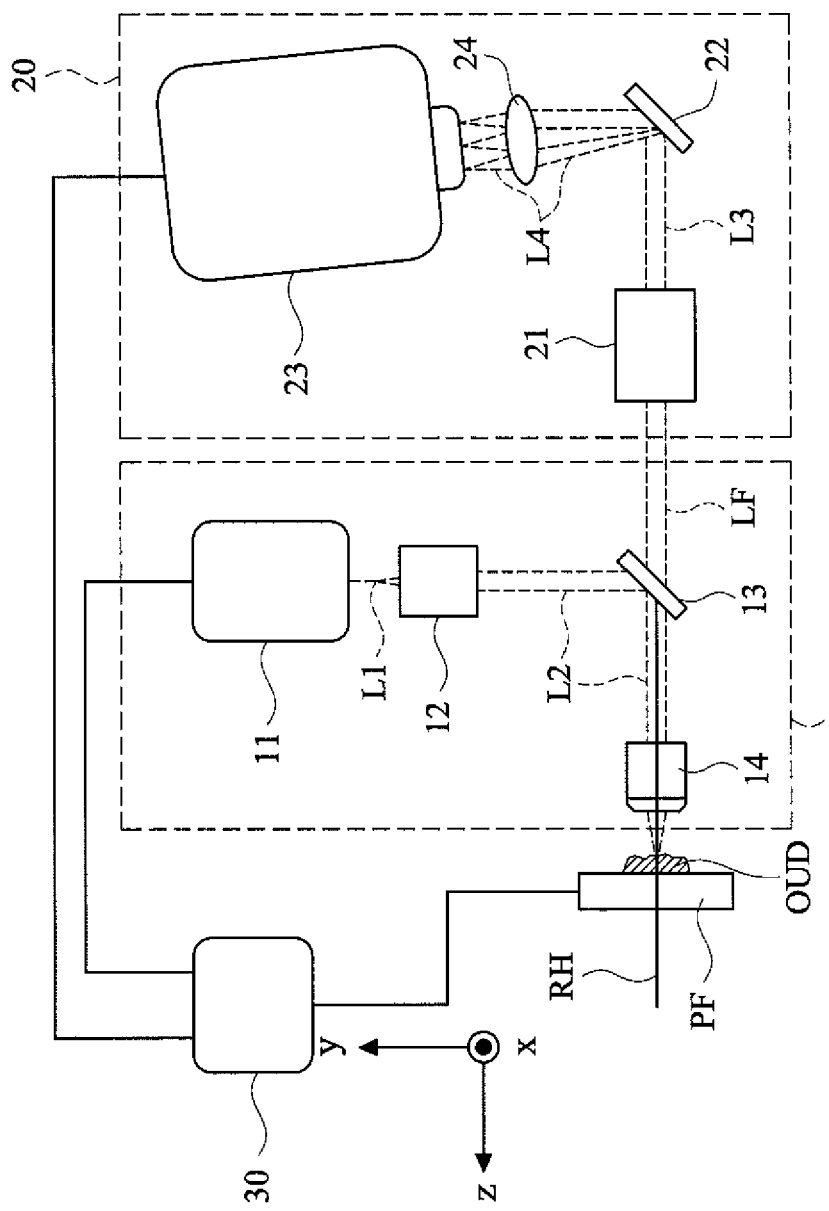
FIG. 1 is a schematic plan view of the fluorescence hyperspectral microscopy system in an embodiment of the present invention that features structured illumination and parallel recording.

Referring to FIG. 1 for an embodiment of the present invention, the fluorescence hyperspectral microscopy system 100 featuring structured illumination and parallel recording includes a light protection sub-system 10, a detection sub-system 20, and an electrical controller 30.

As shown in FIG. 1, the light projection sub-system 10 includes a digital light processing (DLP) module 11, a first lens set 12, an optical path allocation element 13, and an objective lens 14.

As shown in FIG. 1, the DLP module 11 generates and projects linear excitation light L1 as the light source of detection. The linear excitation light L1 projected by the DLP module 11 serves to increase the longitudinal resolution of detection signals and substantially shorten the time required for scan sampling. Performing multi-phase detection with the DLP module 11 further enhances the resolution of the signals and spectrum detected.

The multi-phase detection is a process where the DLP module 11 changes the phase of its linear excitation light L1 at least three times, and where the detection sub-system 20 processes the obtained signals, which correspond to the three phase changes respectively, in order to increase the resolution of the signals and spectrum detected.

As shown in FIG. 1, the first lens set 12 consists of at least one lens. The first lens set 12 condenses the linear excitation light L1 projected by the DLP module 11 into a detection light beam L2 and projects the detection light beam L2 along the same path and direction as the linear excitation light L1.

Referring to FIG. 1 again, the detection light beam L2 projected from the first lens set 12 is reflected by the optical path allocation element 13 and consequently travels along a first path RH. The optical path allocation element 13 can be so arranged that the detection light beam L2 is reflected at an angle of 90 degrees.

Referring again to FIG. 1, the objective lens 14 is provided in the first path RH, receives the detection light beam L2 reflected from the optical path allocation element 13, and focuses the reflected detection light beam L2 onto an object under detection OUD, which is placed on a two-dimensional moving platform PF. As a result, the object under detection OUD generates a back fluorescence signal LF when excited by the detection light beam L2. The objective lens 14 receives the fluorescence signal LF and transmits the fluorescence signal LF to the optical path allocation element 13 along the first path RH such that the fluorescence signal LF passes through the optical path allocation element 13.

The optical path allocation element 13 separates the fluorescence signal LF from the detection light beam L2, which is condensed from the linear excitation light L1 and has a greater wavelength than the fluorescence signal LF, allowing the fluorescence signal LF to enter the detection sub-system 20. The optical path allocation element 13 can be a dichroic beam splitter.

With continued reference to FIG. 1, the detection sub-system 20 includes a second lens set 21, a frequency-dividing reflection element 22, a two-dimensional light detector 23, and a light collection element 24.

As shown in FIG. 1, the fluorescence signal LF passing through the optical path allocation element 13 is incident on the second lens set 21, which modulates the fluorescence signal LF into a corresponding collimated light beam L3 and outputs the collimated light beam L3.

Figure 2:
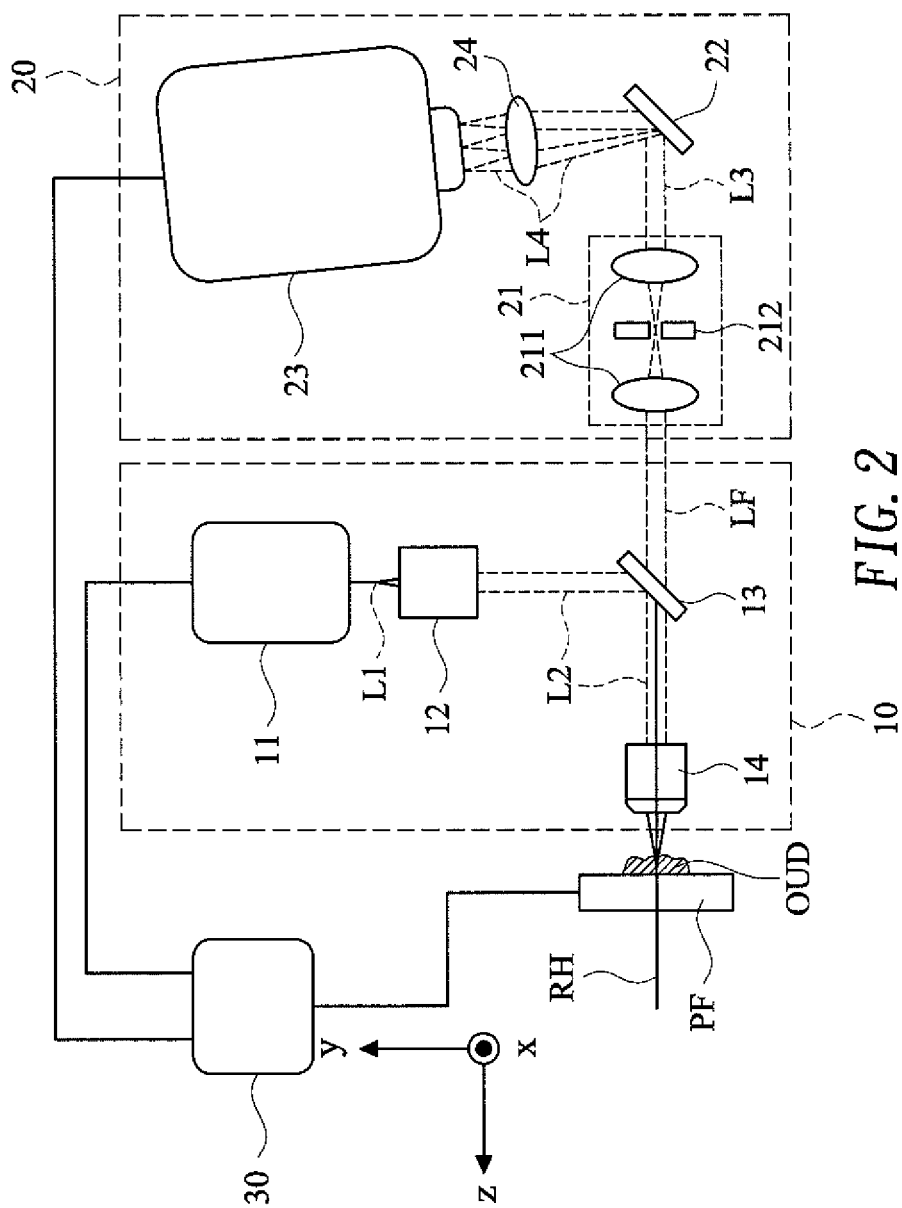
FIG. 2 is another schematic plan view of the fluorescence hyperspectral microscopy system in the embodiment of FIG. 1.

Referring to FIG. 2 in conjunction with FIG. 1, the second lens set 21 may include at least one condenser lens 211 and a cut-off element 212. The cut-off element 212 can be so configured that it allows passage of only an X-axis-direction strip-like portion of the fluorescence signal LF passing through the optical path allocation element 13.

Figure 3:
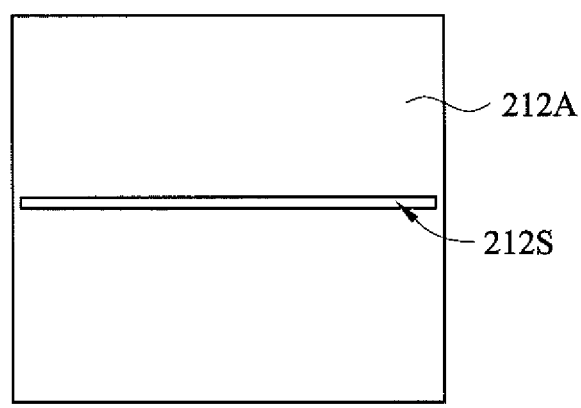
FIG. 3 is a sectional front view of the second lens set in the embodiment of FIG. 1.

The cut-off element 212 can be a light-blocking element 212A with a light-penetrable slit 212S as shown in FIG. 3.

Referring back to FIG. 1, the frequency-dividing reflection element 22 reflects the collimated light beam L3 output by the second lens set 21. More specifically, signals in the collimated light beam L3 that are of different frequencies are reflected at different angles respectively to produce a two-dimensional signal L4.

The frequency-dividing reflection element 22 can be a reflective diffraction grating, a prism, or an acoustic-optic modulator.

Figure 4:
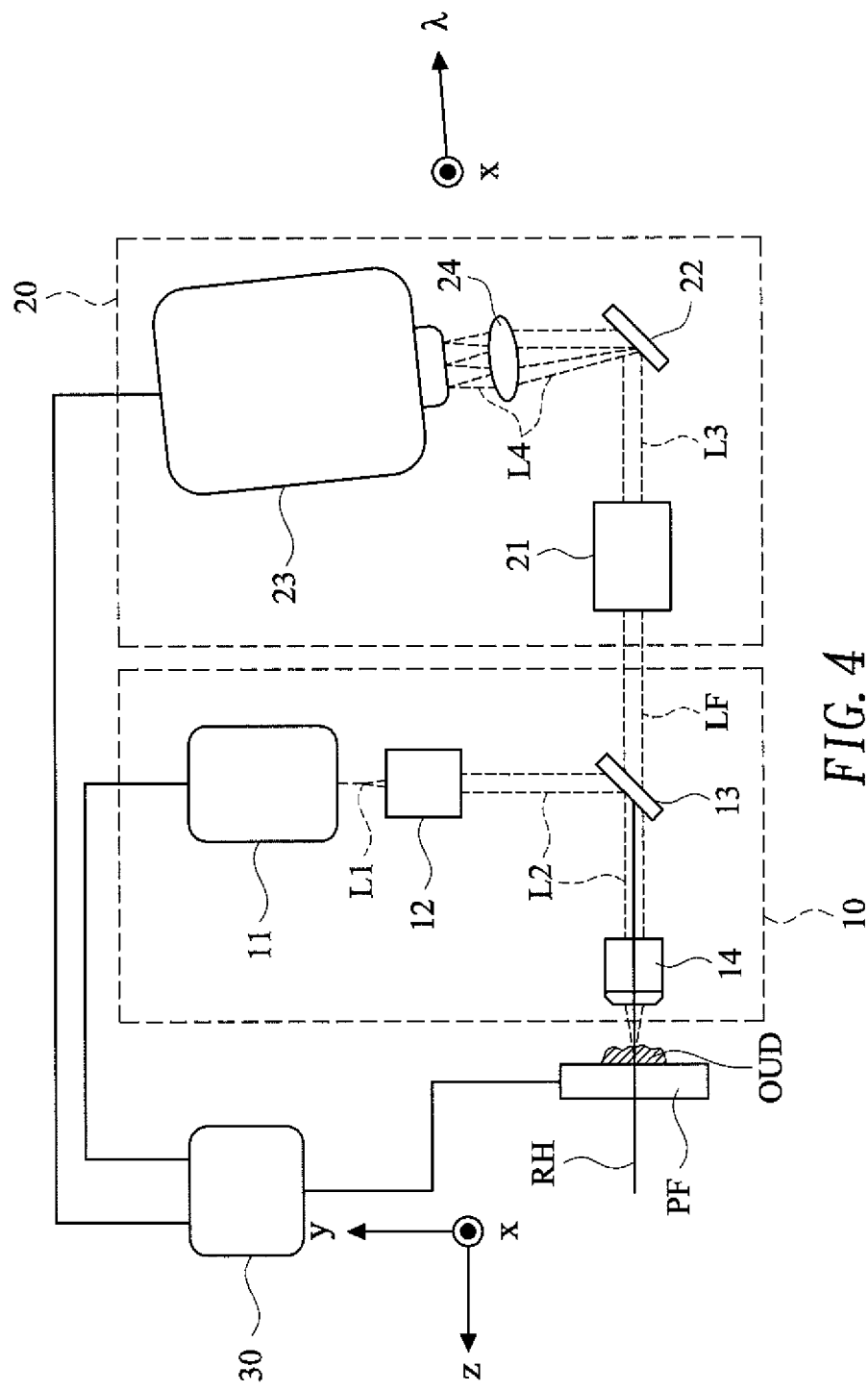
FIG. 4 is yet another schematic plan view of the fluorescence hyperspectral microscopy system in the embodiment of FIG. 1, showing the two reference dimensions of the two-dimensional light detector.

Referring to FIG. 4, the direction in which the collimated light beam L3 fans out is defined as the X-axis direction, so one dimension of the two-dimensional signal L4 corresponds to a distance in the X-axis direction. Moreover, as the frequency-dividing reflection element 22 reflects signals of different frequencies in the collimated light beam L3 at different angles respectively, the other dimension of the two-dimensional signal L4 corresponds to signal distribution over a spectrum and can be represented by either wavelength (λ) or frequency, the former of which is used in this embodiment.

As shown in FIG. 1, the two-dimensional light detector 23 serves to receive the two-dimensional signal L4 reflected from the frequency-dividing reflection element 22. The two-dimensional light detector 23 can be a two-dimensional charge-coupled device (CCD).

Referring again to FIG. 1, the light collection element 24 is provided between the frequency-dividing reflection element 22 and the two-dimensional light detector 23. The light collection element 24 condenses the two-dimensional signal L4 reflected from the frequency-dividing reflection element 22 so that the two-dimensional signal L4 is incident on the two-dimensional light detector 23, and by doing so, the light collection element 24 increases the signal strength of the two-dimensional signal L4 received by the two-dimensional light detector 23.

Figure 5:
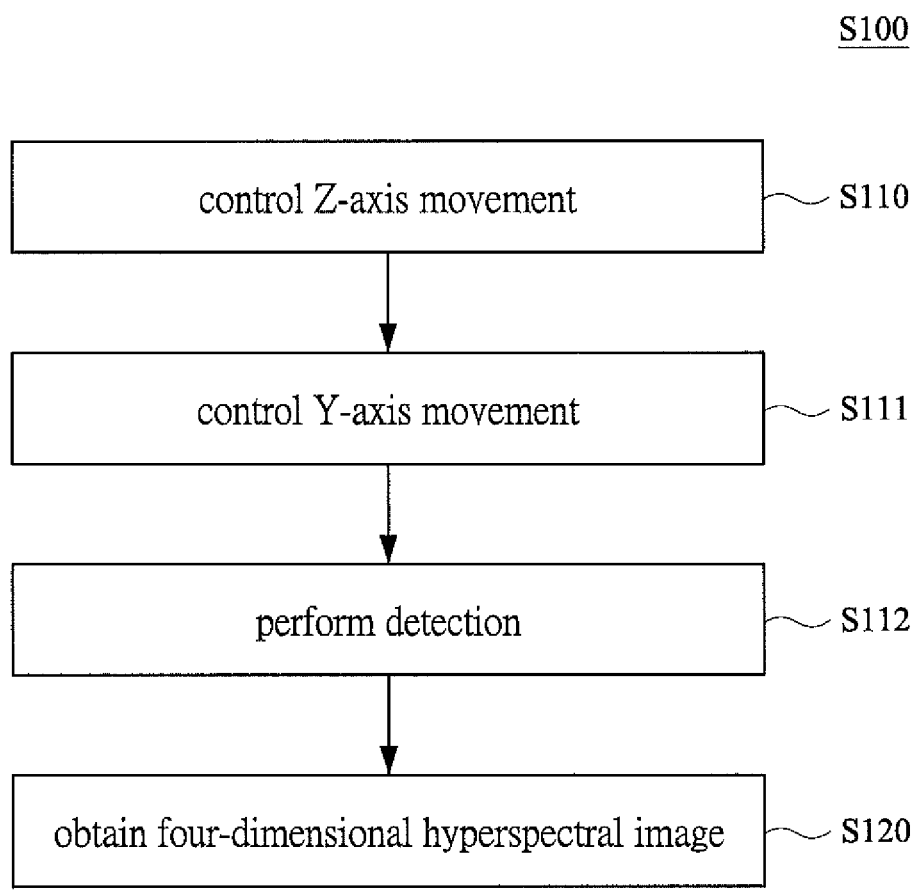
FIG. 5 is a flowchart showing the control steps performed by the electrical controller in the embodiment of FIG. 1.
Figure 6:
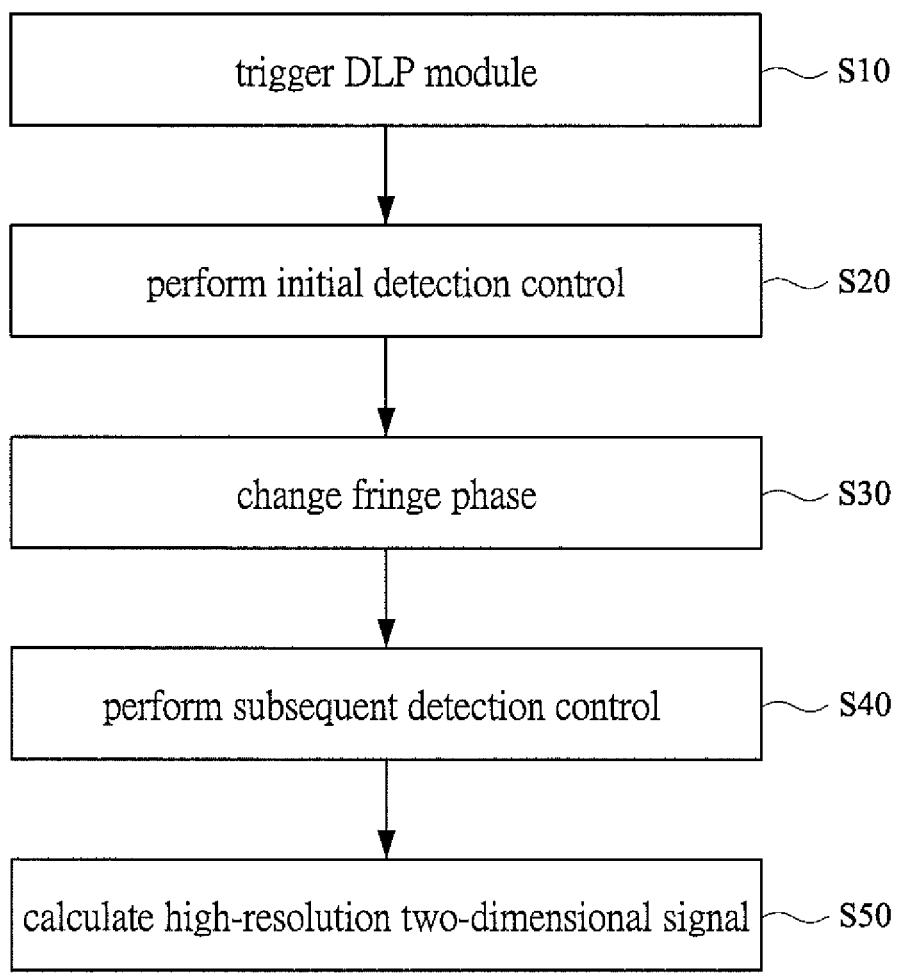
FIG. 6 is a flowchart showing the detection steps performed by the electrical controller in the embodiment of FIG. 1.

Referring to FIG. 1, FIG. 5, and FIG. 6, the electrical controller 30 is electrically connected to and serves to control the DLP module 11, the two-dimensional moving platform PF, and the two-dimensional light detector 23. In addition, the electrical controller 30 performs a control procedure 5100 to ensure that the fluorescence hyperspectral microscopy system 100 featuring structured illumination and parallel recording can accurately obtain information of the object under detection OUD in both spatial and spectral dimensions and produce a four-dimensional hyperspectral image of the object under detection OUD.

As shown in FIG. 5 and FIG. 6, the control procedure S100 includes the steps of: controlling Z-axis movement (step S110), controlling Y-axis movement (step S111), detection (step S112), and obtaining a four-dimensional hyperspectral image (step S120). The step of detection (step S112) includes the sub-steps of: triggering the DLP module (sub-step S10), performing initial detection control (sub-step S20), changing a fringe phase (sub-step S30), performing subsequent detection control (sub-step S40), and calculating a high-resolution two-dimensional signal (sub-step S50).

To control Z-axis movement (step S110), the electrical controller 30 instructs the two-dimensional moving platform PF to stop at a plurality of Z-axis coordinate points sequentially. Whenever the two-dimensional moving platform PF stops at one of the Z-axis coordinate points, the electrical controller 30 performs the step of controlling Y-axis movement (step S111).

More specifically, the step of controlling Y-axis movement (step S111) is performed by the electrical controller 30 instructing the two-dimensional moving platform PF to stop at a plurality of Y-axis coordinate points sequentially. Whenever the two-dimensional moving platform PF stops at one of the Y-axis coordinate points, the electrical controller 30 performs the step of detection (step S112).

The step of detection (S112) is carried out as follows. To begin with, the DLP module 11 is triggered (sub-step S10) by instructing the DLP module 11 to generate the linear excitation light L1 of an initial phase. Then, initial detection control is performed (sub-step S20) by instructing the two-dimensional light detector 23 to receive the two-dimensional signal L4. Next, the fringe phase is changed (sub-step S30) by instructing the DLP module 11 to change the phase of its linear excitation light L1 at least once so that a different phase value is generated each time the phase of the linear excitation light L1 is changed. Then, subsequent detection control is performed (sub-step S40) by instructing the two-dimensional light detector 23 to receive the two-dimensional signal L4 each time a different phase value is generated. After that, a high-resolution two-dimensional signal is calculated (sub-step S50) from the two-dimensional signals L4 corresponding respectively to the initial phase and the subsequent phase value(s). This high-resolution two-dimensional signal L4 is a high-resolution signal of the object under detection OUD and has one dimension corresponding to a distance in the X-axis direction and the other dimension corresponding to spectral distribution.

Thus, high-resolution signal data regarding the object under detection OUD in four dimensions (corresponding to the X-axis, the Y-axis, the Z-axis, and spectral distribution respectively) are obtained.

Lastly, as shown in FIG. 5, a four-dimensional hyperspectral image is obtained (step S120) by the electrical controller 30 instructing the two-dimensional light detector 23 to record, store, or transmit the four-dimensional hyperspectral image obtained of the object under detection OUD. The four-dimensional hyperspectral image contains four-dimensional data of the object under detection OUD, wherein the four dimensions correspond to the X-axis, the Y-axis, the Z-axis, and spectral distribution respectively.

The embodiments described above are intended only to demonstrate the technical concept and features of the present invention so as to enable a person skilled in the art to understand and implement the contents disclosed herein. It is understood that the disclosed embodiments are not to limit the scope of the present invention. Therefore, all equivalent changes or modifications based on the concept of the present invention should be encompassed by the appended claims.

What is claimed is:

1. A fluorescence hyperspectral microscopy system featuring structured illumination and parallel recording, comprising:
    a light projection sub-system comprising:
        a digital light processing (DLP) module for generating and projecting linear excitation light;
        a first lens set consisting of at least one lens and configured to condense the linear excitation light into a detection light beam;
        an optical path allocation element for reflecting the detection light beam in order for the detection light beam to propagate along a first path; and
        an objective lens provided in the first path and configured to receive the detection light beam, focus the detection light beam onto an object under detection on a two-dimensional moving platform, receive a fluorescence signal reflected from the object under detection when the object under detection is excited by the detection light beam, and transmit the fluorescence signal along the first path to the optical path allocation element such that the fluorescence signal passes through the optical path allocation element;
    a detection sub-system comprising:
        a second lens set on which the fluorescence signal passing through the optical path allocation element is incident and which modulates the fluorescence signal to a corresponding collimated light beam and outputs the collimated light beam;
        a frequency-dividing reflection element for reflecting signals of different frequencies in the collimated light beam at different angles respectively to produce a two-dimensional signal;
        a two-dimensional light detector for receiving the two-dimensional signal; and
        a light collection element provided between the frequency-dividing reflection element and the two-dimensional light detector and configured to condense the two-dimensional signal onto the two-dimensional light detector; and
    an electrical controller electrically connected to and configured to control the DLP module, the two-dimensional moving platform, and the two-dimensional light detector, the electrical controller also being configured to perform a control procedure.

2. The fluorescence hyperspectral microscopy system of claim 1, wherein the control procedure comprises the steps of;
    controlling Z-axis movement, by the electrical controller instructing the two-dimensional moving platform to stop sequentially at a plurality of Z-axis coordinate points, the electrical controller further performing a step of controlling Y-axis movement when the two-dimensional moving platform stops at each of the Z-axis coordinate points; and
    obtaining a four-dimensional hyperspectral image of the object under detection, by the electrical controller instructing the two-dimensional light detector to record, store, or transmit the four-dimensional hyperspectral image, the four-dimensional hyperspectral image having data of the object under detection in four dimensions, the four dimensions corresponding to an X-axis, a Y-axis, a Z-axis, and spectral distribution respectively;

wherein the step of controlling Y-axis movement is performed by the electrical controller instructing the two-dimensional moving platform to stop sequentially at a plurality of Y-axis coordinate points, the electrical controller further performing a step of detection when the two-dimensional moving platform stops at each of the Y-axis coordinate points, the step of detection comprising the sub-steps of:

triggering the DLP module, by instructing the DLP module to generate the linear excitation light of an initial phase;

performing initial detection control, by instructing the two-dimensional light detector to receive the two-dimensional signal;

changing a fringe phase, by instructing the DLP module to change a phase of the linear excitation light at least once so that a different phase value is generated each time the phase of the linear excitation light is changed;

performing subsequent detection control, by instructing the two-dimensional light detector to receive the two-dimensional signal each time a different said phase value is generated; and calculating a high-resolution two-dimensional signal from the two-dimensional signals corresponding respectively to the initial phase and the different phase value(s), wherein the high-resolution two-dimensional signal is a high-resolution signal of the object under detection and has one dimension corresponding to a distance in an X-axis direction and another dimension corresponding to spectral distribution.

3. The fluorescence hyperspectral microscopy system of claim 1, wherein the optical path allocation element is a dichroic beam splitter.

4. The fluorescence hyperspectral microscopy system of claim 1, wherein the second lens set includes at least one condenser lens and a cut-off element, the cut-off element allowing passage of only an X-axis-direction strip-like portion of the fluorescence signal passing through the optical path allocation element.

5. The fluorescence hyperspectral microscopy system of claim 4, wherein the cut-off element is a light-blocking element with a light-penetrable slit.

6. The fluorescence hyperspectral microscopy system of claim 4, wherein the two-dimensional signal has one dimension corresponding to a distance in the X-axis direction and another dimension corresponding to spectral distribution.

7. The fluorescence hyperspectral microscopy system of claim 5, wherein the two-dimensional signal has one dimension corresponding to a distance in the X-axis direction and another dimension corresponding to spectral distribution.

8. The fluorescence hyperspectral microscopy system of claim 1, wherein the frequency-dividing reflection element is a reflective diffraction grating, a prism, or an acoustic-optic modulator.

9. The fluorescence hyperspectral microscopy system of claim 1, wherein the two-dimensional light detector is a two-dimensional charge-coupled device (CCD).

* * * * *